(12) United States Patent
Olovson

(10) Patent No.: US 6,558,360 B1
(45) Date of Patent: May 6, 2003

(54) SYRINGE PROTECTION CAP

(76) Inventor: Gudmar Olovson, 64, rue Saint Charles, F-75015 Paris (FR)

( * ) Notice: Subject to any disclaimer, the term of this patent is extended or adjusted under 35 U.S.C. 154(b) by 0 days.

(21) Appl. No.: 09/508,643

(22) PCT Filed: Sep. 18, 1998

(86) PCT No.: PCT/SE98/01673

§ 371 (c)(1),
(2), (4) Date: Mar. 15, 2000

(87) PCT Pub. No.: WO99/17822

PCT Pub. Date: Apr. 15, 1999

(65) Prior Publication Data (65)

(30) Foreign Application Priority Data

Sep. 22, 1997 (SE) .................................................. 9703411

(51) Int. Cl.⁷ .................................................. A61M 5/00
(52) U.S. Cl. ..................................................... 604/263
(58) Field of Search ............................. 604/263, 93.01, 604/192, 193, 197

(56) References Cited

U.S. PATENT DOCUMENTS

| | | | |
|---|---|---|---|
| 2,571,653 A | 10/1951 | Bastien | |
| 4,192,919 A * | 3/1980 | Raghavachari | 137/199 |
| 4,425,120 A | 1/1984 | Sampson et al. | |
| 4,631,057 A | 12/1986 | Mitchell | |
| 4,812,293 A * | 3/1989 | McLaurin et al. | 210/321.75 |
| 5,009,642 A * | 4/1991 | Sahi | 604/110 |
| 5,116,326 A | 5/1992 | Schmidt | |
| 5,147,309 A * | 9/1992 | Hemmerich et al. | 604/122 |
| 5,154,698 A | 10/1992 | Compagnucci et al. | |
| 5,239,981 A * | 8/1993 | Anapliotis | 600/122 |
| 5,267,977 A * | 12/1993 | Feeney, Jr. | 604/198 |
| 5,531,707 A * | 7/1996 | Kers et al. | 222/541.6 |
| 5,645,530 A * | 7/1997 | Boukhny et al. | 604/175 |
| 5,843,047 A * | 12/1998 | Pyrozyk et al. | 604/192 |
| 6,213,994 B1 * | 4/2001 | Jansen et al. | 215/253 |

* cited by examiner

Primary Examiner—Teresa Walberg
Assistant Examiner—Daniel Robinson
(74) Attorney, Agent, or Firm—Banner & Witcoff, Ltd.

(57) ABSTRACT

A needle protection device for a hypodermic syringe in which the syringe includes a container, a plunger which can be reciprocated in the container by a rod, and needle secured to the container, comprises a tubular member and a membrane. The tubular member has an open end that snugly fits over the container and a length that is greater than the length of the needle. The membrane seals the free end of the tubular member to protect the health care professional from injury. The membrane is positioned within the tubular member at a location spaced from the end surface of the tubular member.

16 Claims, 1 Drawing Sheet

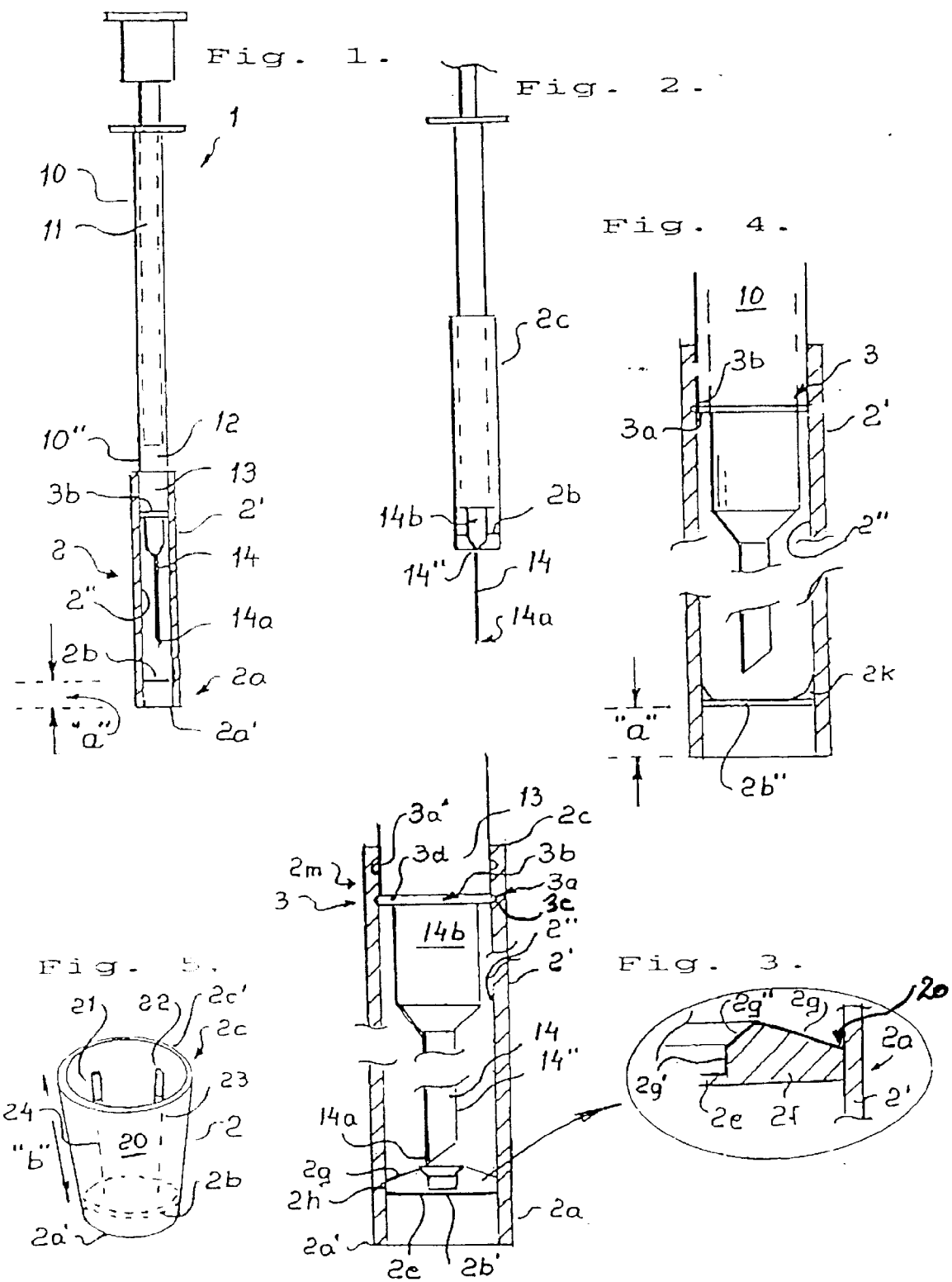

SYRINGE PROTECTION CAP

FIELD OF INVENTION

The present invention relates to a needle protection device or cap adapted for co-action with an hypodermic syringe that includes a container, a plunger which can be moved reciprocatingly in said container by means of a rod, and a needle which is fixed to or fastenable to one end-part of the container.

The needle protection device basically includes a tubular member, normally a tubular member of circular cross-section, whose axial length is slightly grater than the length of the needle.

More particularly, the present invention relates to a needle protection device that has an inner, radial-related cross-section which corresponds or at least essentially corresponds to the outer radial-related cross-section of the container.

This cross-section dimensioning of the needle protection device enables said device to be arranged for axial movement relative to the container, from a position in which the needle is covered by the device to a position in which said needle is exposed, or vice versa.

DESCRIPTION OF THE BACKGROUND ART

There has long been a desire to protect people who handle hypodermic syringes (either for injection and/or aspiration purposes) against accidental injury (prick-injuries), and several different designs of needle protectors have been proposed to this end.

These needle protectors are usually displaceably or removably mounted to the container of the syringe and are designed to cover the needle and the needle point.

The needle protector is removed prior to injection and/or aspiration, so as to expose the needle and its point.

For the sake of simplicity, the following description is concerned solely with the injection of liquids, although it will be understood that the concepts of the invention are equally as applicable to the aspiration of fluids.

A needle which remains exposed after an injection has been given can very well be contaminated and therewith transmit serious sicknesses to a person who is accidentally injured by the exposed needle and its point.

Various different types of needle protectors which protect people against accidental injury are known to the art. Such protectors basically include a tubular member that has a protective seal fitted on its free end.

A needle protector of this kind will have the form of a sleeve which can be readily removed from the syringe immediately prior to an injection. This sleeve must be kept separate during the injection process and replaced by hand over the needle upon completion of the injection, so as to shield the needle against unintentional contact therewith.

The sleeves, or tubular members, of this type of needle protector are dimensioned at their open part for secure but easily released co-action with the part of the needle attached to the container.

Other known needle protection constructions are movable over the container and co-act therewith during the injection, said syringe and said needle protecting means together forming a unit.

The present invention relates to this category of needle protection means.

Earlier known hypodermic syringe constructions that include needle protection means within this category have been described and illustrated in the following patent publications:

U.S. Pat. No. 4,425,120

This publication teaches a needle protection device (19) which in a first position covers the needle (15) and the needle point (25), and in a second, upwardly moved position exposes the needle and the needle point.

The needle protection device (19) has the form of a tubular member that has at its free end a hole (41) which is large enough to allow a needle holding element (24) or a needle protection device (29) to pass through.

The hole (41) may be covered with a material that is split by the needle (15) and/or the needle protection device (29). The covering material functions as a sealing end-region of the tubular needle protection device and serves to seal the end-related edge or end surface of the tubular member.

U.S. Pat. No. 2,571,653

This publication teaches a needle protection device (1) which can be moved reciprocatingly between fixed positions, i.e. between a needle covering position and a needle exposing position. The free end of the needle protection device (1) is conical and has a central opening which is adapted to embrace the needle attachment (4).

U.S. Pat. No. 4,725,267

This publication teaches a needle protection device which includes an opening, i.e. a hole (58), and the free end (56) of the needle protection device (60) corresponds to the needle cross-section.

SUMMARY OF THE INVENTION

Technical Problems

When taking into consideration the technical deliberations that a person skilled in this particular art must make in order to provide a solution to one or more technical problems that he/she encounters, it will be seen that on the one hand it is necessary initially to realise the measures and/or the sequence of measures that must be undertaken to this end, and on the other hand to realise which means is/are required to solve one or more of said problems. On this basis, it will be evident that the technical problems listed below are highly relevant to the development of the present invention.

In the case of a needle protection device which in a needle covering position co-acts with the container and which when moved over the container allows the point of the needle to penetrate through the bottom of said device, and which upon completion of an injection or some corresponding process can be moved to a needle protecting position, it will be seen when considering the present state of the art as described above that a problem resides in providing conditions with the aid of simple means that will enable a membrane which sealingly covers the cross-sectional area of the tubular member of said device to be placed in a position where it is well protected from externally acting forces.

It will also be seen that a technical problem resides in producing with simple means a needle protection device, in the form of a tubular member, that will enable a thin membrane to be placed in a well protected position.

It will also be seen that a technical problem resides in the provision of conditions, with simple means, which enable a thin, tough, membrane element to be formed within the tubular member at an adapted distance from the end-region of the needle protection device.

It will also be seen that a technical problem is one of providing conditions which enable a first end-part of the tubular member that lies distal from the membrane to be provided with a first part of a two-part coupling element active between the tubular member and the container and having the form of one or more inner radially-related and/or axially-related grooves.

Another technical problem is one of realising the significance of and the advantages afforded by providing a second part of said coupling element on the container in the form of a radially related and/or axially related edge, and to position said edge at or adjacent to said first end-part.

Another technical problem is one of realising the significance of and the advantages afforded by giving the material from which the tubular member is made and the dimensions of said tubular member, at least in the vicinity of said first end-part, properties that will allow the tubular member to expand over said edge as it is moved along the container.

It will also be seen that a further technical problem is one of realising the significance of and the advantages associated with positioning the membrane within the tubular member at an adapted distance from the end surface of said member and integrating the membrane with the tubular member in general.

Another technical problem is one of realising the significance of and the advantages associated with constructing the needle protection device in a manner which will enable the hypodermic needle to be bent whilst protected by said protection device, therewith to eliminate the risk of accidental damage by the needle and/or to render the needle unusable after having completed an injection.

Solutions

The present invention takes as its starting point a needle protection device adapted for use with an hypodermic syringe which includes a container, a plunger that can be moved reciprocatingly in said container by means of a rod, and a needle which is fixed to or fastenable to one end-part of the container, said needle protection device having basically the form of a tubular member whose axial length is slightly greater than the length of the needle and which includes the features mentioned in the introduction in other respects.

With the intention of solving one or more of the aforesaid a technical problems, it is proposed in accordance with the invention that said tubular member shall include a thin membrane which covers the cross-sectional area of said member and which shall be placed at an adapted distance from the end-related edge or end-surface of the tubular member.

According to proposed embodiments that lie within the scope of the inventive concept, it is proposed that a first end-part of the tubular member lying distal from the membrane is provided with a first part of a two-part coupling element between the tubular member and the container.

According to one embodiment, this first part is comprised of an inner radially-related and/or axially-related groove.

According to another embodiment, a second coupling-part is comprised of a radially-related and/or axially-related edge, where said edge is positioned at or adjacent to said end-part.

It is particularly proposed that the material from which the tubular member is made and the dimensioning of said tubular member, at least in the vicinity of the first end-part, imparts to said member properties that will enable it to expand over said edge.

It is also proposed that a first end-part of the tubular member lying distal from the membrane is provided with two first coupling-parts included in a two-part coupling arrangement, where said two parts are axially displaced from one another.

It is also proposed that the membrane shall be protected by the tubular member, by placing said membrane within the tubular member at a small distance from the end surface of said member, and that said membrane has a ring-shaped edge.

Advantages

Those advantages primarily obtained with a needle protection device adapted for a hypodermic syringe in accordance with the present invention reside in the provision of features which enable the needle protection device to be moved readily along the container of the syringe, said needle protection device being provided with a membrane which seals the cross-sectional area of the end-part that lies distal from the container and which ensures that the needle and point of said needle will be effectively covered by the protection device, and that when the protection device is moved along the container the point of the needle will penetrate the membrane and therewith expose the needle, and where upon completion of an injection or some corresponding process the needle protection device can be moved back to a needle covering position.

A particular advantage is that the membrane is protected against the effect of externally acting forces and is positioned within the tubular member at a distance from the end-related edge or end-surface of the tubular member, for example.

The primary characteristic features of a needle protection device adapted for an hypodermic syringe in accordance with the present invention are set forth in the characterising clause of the following claim 1.

BRIEF DESCRIPTION OF THE DRAWINGS

The present invention will now be described in more detail with reference to preferred exemplifying embodiments thereof and also with reference to the accompanying drawings, in which FIG. 1 is a side view of an hypodermic syringe that includes a needle protection device in accordance with the invention, and shows the protection device in a needle protecting position;

FIG. 2 illustrates the syringe of FIG. 1 and shows the needle protection device moved to a position along the syringe container to a position in which the needle is exposed.;

FIG. 3 is a slightly enlarged part of the FIG. 1 illustration and shows the co-action between the needle protection device and the container through the medium of a two-part coupling element, and also shows one membrane embodiment;

FIG. 4 illustrates another embodiment of the two-part coupling element, and also shows an alternative membrane embodiment; and FIG. 5 is a perspective view of an alternative embodiment of the needle protection device.

DESCRIPTION OF EMBODIMENTS AT PRESENT PREFERRED

FIG. 1 is a side view of an hypodermic syringe 1 to which there is fitted a needle protection device 2 constructed in accordance with the invention.

The illustrated syringe 1 includes a container 10 and a plunger 12 which is reciprocatingly movable in said container by means of a rod 11.

A needle 14 is connected permanently to one end 13 of the container, although in certain cases the needle may be a separate unit that can be attached to said container.

As will be seen from FIG. 1, the needle protection device 2 has the basic form of a tubular member which has a circular cross-section and the axial length of which is slightly longer than the length of the needle 14.

The length of the device is adapted so that in addition to covering the needle 14, the device 2 will also cover the aforesaid end-part 13 of said container and provide a free space in the vicinity of the point 14a of said needle.

The needle protection device 2 is comprised substantially of a tubular part 2' whose inner radial-related cross-section is adapted to correspond to, or at least essentially to correspond to an outer radial-related cross-section of the container 10.

The needle protection device 2, in the form of said tubular part 2', among other things, can be moved axially in relation to the container 10 from a position in which it covers the needle 14, as shown in FIG. 1, to a position in which it exposes the needle, as shown in FIG. 2, or vice versa.

The end 2a of the device 2 distal from the container 10 carries a thin membrane 2b which seals across the inner cross-sectional area of the tubular part.

By thin membrane 2b is meant a membrane whose thickness is considerably thinner than the thickness of the wall of the tubular part 2'.

The needle protection device is comprised essentially of a tubular section that has a circular cross-sectional shape and a constant radius, and said membrane 2b that seals and/or covers said cross-sectional area of the tubular part.

The inner circular surface 2" of the tubular part 2' is adapted for light frictional co-action with the outer circular surface 10" of the container 10.

The membrane 2b shall be made from a plastic material of such thickness that when the tubular part 2' is moved along the container 10 so as to expose the needle 14 (FIG. 2), the point 14a of said needle will be able to penetrate the membrane 2b and therewith make the syringe 1 ready for use, either for injecting liquid contained in the container 10 or for aspiring a liquid sample for analysis purposes.

With regard to the properties of the membrane material, these properties will conveniently coincide with the properties of the material from which the tubular member is made, and the needle protection device will conveniently be manufactured in one single operation.

The membrane 2b will conveniently have a thickness smaller than 0.5 mm, preferably between 0.1 and 0.3 mm, and the properties of said material shall be capable of enabling the peripheral edge region of an opening formed by the needle point 14a to lie sealingly against the outer surface 14" of said needle 14.

The elasticity of the membrane material shall also be such as to enable the membrane 2b to stretch around the needle fastening part 14b as illustrated in FIG. 2, without splitting or rupturing.

Various alternative embodiments of the membrane 2b will be described hereinafter with reference to FIGS. 3 and 4.

A first end-part 2c of the tubular member 2' that lies distal from the membrane 2b is provided with a first part 3a of a two-part coupling element 3 between the tubular member 2' and the container 10.

As shown in FIG. 3, the first coupling part 3a is comprised of an inner, radial-related groove 3c in the tubular member 2'.

A second coupling part 3b belonging to the container 10 is comprised of a radial-related edge 3d.

The edge 3d is positioned in or adjacent to said end-part 13, more specifically in the junction between said end-part 13 and a fastener part 14b.

The material from which the tubular member 2' is made and the dimensioning of said tubular member, at least with regard to the first end-part 2c, are such as to enable the tubular member 2' to expand over said edge 3d during axial movement of said tubular member.

A first end-part 2m (2c) of the tubular member 2' located distal from the membrane 2b is provided with two first parts 3a, 3a' which form a two-part coupling means 3 and which are displaced axially with respect to one another.

Although the illustrated embodiment includes radial-related grooves, it will be understood that the coupling means may consist in an axially related groove or in axially related grooves with or without axially related ridges, or vice versa (see FIG. 5).

The membrane 2b is positioned in the tubular member 2' at a distance of about 2–10 mm, preferably 3–5 mm, from the end 2a or end-surface 2a' of the tubular member, although this distance will be greater for needle protecting devices of larger diameter.

From the aspect of manufacture, it is convenient to place the first coupling part 3a and 3a' on the inside of the tubular member 2' in the form of a groove, while retaining the edge 3d in the form shown in FIG. 3.

FIG. 4 is an illustration corresponding to the illustration of FIG. 3, although with the difference that the coupling between the first part 3a and the second part 3b of the two-part coupling means 3 is achieved by dimensional adaptation of the container surface 10" and the surface 2" of the tubular member 2' so as to obtain a frictional fit between said surfaces and therewith generate a predetermined resistance when moving the tubular member 2' relative to the container 10.

The invention is also based on a particular construction of the membrane 2b.

In the case of the embodiment illustrated in FIGS. 1 and 2, the tubular member 2' and the membrane 2b are formed integrally in a one-piece structure in one single manufacturing operation and also from one and the same plastic material. The individual properties of the membrane 2b and the tubular member 2' are obtained by adapting the thickness of the material to this end.

The membrane 2b and/or a peripheral edge-ring may, of course, be manufactured as a separate unit and inserted into a tubular member 2'.

A first integrated or unit-manufactured membrane unit 2b' is shown in FIG. 3, while a second integrated or unit manufactured membrane unit 2b' is shown in FIG. 4. The membrane 2b' shown in FIG. 3 includes a central part 2e that has a thin membrane layer, and a ring-shaped part 2f which embraces the central part 2e and which is fastened to or formed integrally with the tubular member 2'.

The thin membrane layer 2e has a surface extension which conforms to the cross-section of the needle 14 or which is slightly larger than said needle cross-section and includes the aforesaid properties.

The membrane layer 2e is fastened to or formed integrally with the ring-shaped part 2f, which has a pronounced triangular cross-sectional shape.

In the illustrated case, a first axially related cylinder-shape surface 2g' is adapted to function as a guide surface for the needle point 14a and the outer surface 14" of the needle 14.

An inwardly conical surface 2g" adjacent the surface 2g' is adapted to function as a guide surface for the needle point 14a, so as to steer said point in towards the surface 2g" should it deviate from a centre line.

An outermost located conical surface 2g slopes slightly outwards, so that after using the syringe, the needle protection device 2 can be used to bend the needle 14, by forcing the pointed part of the needle against a part 2o of the circular corner 2h.

In order to make this possible, when the protection device 2 is in its retracted position, shown in FIG. 1, the device shall be tilted away from its centre line and rotated relative to the container 10 around the centre line as it is moved up over said container.

FIG. 4 shows the membrane 2b" connected to the inner surface 2" of the tubular member 2' through the medium of a ring-shaped reinforcement 2k.

The device 2 may conveniently be made of a transparent material so as to enable a scale on the container of said syringe to be clearly seen through said device when the device is in its retracted position (FIG. 2).

There is nothing to prevent certain parts of the device from being coloured, for instance coloured red. In this respect, the device may be provided with axially extending coloured strips between which the scale divisions can be seen and easily read.

The needle point 14a may be located at a distance of 1–7 mm from the membrane 2b in the position of the needle shown in FIG. 1, preferably a distance of 2–4 mm.

FIG. 5 is a perspective schematic illustration of an alternative needle protection device. The device includes an upper part 2c which is provided with a number of axially extending ridges, in the illustrated case four symmetrically orientated ridges 21, 22, 23 and 24, which form axial slide surfaces against the outer surface 10" of the container 10.

These ridges may also be from two to three in number or may be more than the illustrated four ridges and may have a height of 0.01–0.2 mm, preferably about 0.1 mm (this height in the illustrated case being calculated from the inner circular surface of the needle protection device and in towards its centre), and a length "b" conforming to the length between the membrane 2b and the upper edge 2c' or the proximity of said edge.

By way of a further alternative, it is shown in FIG. 5 that the length "b" may be much shorter, for instance roughly 10% of the total length of the device.

The needle protection device 2 may be formed from a material that is slightly coloured, such as a reddish colour, and may include at least adjacent the scale on the container a longitudinally extending section 20 that is completely transparent.

It will be understood that the invention is not restricted to the aforedescribed and illustrated exemplifying embodiments thereof and that modifications are possible within the scope of the inventive concept as defined in the following claims.

We claim:

1. A needle protection device adapted for use with a hypodermic syringe which includes a container, a plunger that can be reciprocated in said container by means of a rod, and a needle secured to one end-part of said container, wherein the needle protection device comprises a tubular member with an axial length that is slightly greater than an axial length of the needle, wherein said tubular member has an inner radial-related cross-sectional shape that substantially corresponds to an outer radial-related cross-sectional shape of the container, and an open first end that is adapted to be snugly received over the container, wherein said tubular member when received over the container is movable axially relative to the container between a position in which the tubular member covers the needle and a position in which the needle is exposed, wherein the tubular member has a second end opposite the first end that is distal from the container, wherein the second end includes an end surface and a membrane which extends completely across the entire cross-sectional area of the tubular member to close and seal the cross-sectional area of said tubular member, wherein said membrane has a thickness which will enable the point of the needle to penetrate said membrane when the tubular member is moved along said container to expose said needle, and wherein the membrane is positioned so as to cover the cross-sectional area of said tubular member at a position spaced inwardly from the end surface of said tubular member.

2. A needle protection device according to claim 1, wherein the first end of the tubular member located distal from the membrane is provided with a first pat of a two-part coupling element between the tubular member and said container.

3. A needle protection device according to claim 2, wherein said first part includes at least one of an inner radially related groove or edge and an axially related groove or edge.

4. A needle protection device according to claim 2, wherein the second part of the two-part coupling element includes at least one of a radially related edge or groove and an axially related edge or groove on said container.

5. A needle protection device according to claim 1, wherein the container includes an edge at the one end-part where the needle is secured, and wherein the first open end of the tubular member is positioned over the edge.

6. A needle protection device according to claim 5, wherein the tubular member is made of a material and is dimensioned at least adjacent the first end so as to enable the tubular member to expand over said edge.

7. A needle protection device according to claim 1, wherein the first end distal from the membrane includes two first parts of a two-part coupling arrangement, with said two first parts are axially displaced from one another.

8. A needle protection device according to claim 1, wherein said membrane is positioned within the tubular member at a distance from the end surface of said tubular member from 2–10 mm.

9. A needle protection device according to claim 1, wherein said membrane is fastened to the tubular member through a ring-shaped reinforcement positioned within the tubular member.

10. A needle protection device according to claim 1, wherein said device is formed from a transparent plastic material.

11. A needle protection device according to claim 1, wherein means for securing the membrane within the tubular member is received within the tubular member.

12. A needle protection device according to claim 1, wherein the membrane and the tubular member are molded as a single member.

13. A needle protection device according to claim 12, wherein the membrane has a first thickness and the tubular member has a second thickness that is greater than the first thickness.

14. A needle protection device according to claim 1, wherein the membrane includes a thickened portion adjacent the tubular member.

15. A needle protection device according to claim 14, wherein the thickened portion of the membrane has a tapered surface to guide the needle to the central portion of the membrane.

16. A needle protection device according to claim 14, wherein the thickened portion of the membrane has a tapered surface sloping away from the needle as the surface extends radially outward to guide the needle into a corner of the membrane after the syringe has been used.

* * * * *